(12) United States Patent
Onishi et al.

(10) Patent No.: US 7,524,312 B2
(45) Date of Patent: Apr. 28, 2009

(54) DISPOSABLE DIAPER

(75) Inventors: Kazuaki Onishi, Kagawa-ken (JP); Yasushi Sayama, Kagawa-ken (JP); Hiroyuki Tanji, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 304 days.

(21) Appl. No.: 10/054,825

(22) Filed: Jan. 23, 2002

(65) Prior Publication Data
US 2002/0099351 A1  Jul. 25, 2002

(30) Foreign Application Priority Data
Jan. 23, 2001  (JP)  ............... 2001-014627

(51) Int. Cl.
*A61F 13/15* (2006.01)
(52) U.S. Cl. .................. 604/385.19; 604/385.101
(58) Field of Classification Search .......... 604/385.101, 604/385.09, 385.14, 385.19, 378
See application file for complete search history.

(56) References Cited

U.S. PATENT DOCUMENTS 5,558,660 A * 9/1996 Dreier .................. 604/385.19
5,897,544 A * 4/1999 Ronnberg .............. 604/385.19
6,114,597 A * 9/2000 Romare .................. 604/378
6,121,510 A   9/2000 Sauer
6,425,889 B1 * 7/2002 Kitaoka et al. ......... 604/385.01
6,699,228 B1 * 3/2004 Chmielewski et al. . 604/385.28
6,921,394 B2 * 7/2005 Sayama et al. ......... 604/385.19

FOREIGN PATENT DOCUMENTS

| EP | 0 998 891 | 5/2000 |
| JP | 1996-196565 A | 8/1996 |
| WO | WO 99/63921 | 12/1999 |

OTHER PUBLICATIONS

Patent Abstracts of Japan, vol. 1996, No. 12, Dec. 26, 1996, & JP 8 196545 (Uni Charm Corp), Aug. 6, 1996.

* cited by examiner

*Primary Examiner*—Tatyana Zalukaeva
*Assistant Examiner*—C. Lynne Anderson
(74) *Attorney, Agent, or Firm*—Butzel Long

(57) ABSTRACT

A disposable diaper includes a basic absorbent batt structure having front and rear waist regions and a crotch region, a pair of barrier cuffs extending along opposite sides of the basic absorbent batt structure and at least one supplementary absorbent batt structure placed on the front waist region of the basic absorbent batt structure between the barrier cuffs. The supplementary absorbent batt structure has a proximal end portion thereof joined to the front waist region of the basic absorbent batt structure and has the vicinity of a distal end portion thereof joined to the vicinities of the barrier cuffs.

11 Claims, 10 Drawing Sheets

DISPOSABLE DIAPER

BACKGROUND OF THE INVENTION

This invention relates to a disposable diaper for absorption and containment of body wastes and the like.

Japanese Patent Application Publication No. 1996-196565A discloses a disposable diaper comprising a liquid-pervious topsheet, a liquid-impervious backsheet and a liquid-absorbent core disposed between these sheet. The core consists of upper and lower cores. The upper core comprises, in turn, a front core extending from a front waist region toward a crotch region and a rear core extending from a rear waist region toward the crotch region. In the known diaper, a rear end of the front core and a front end of the rear core are spaced from each other by a given dimension in the crotch region in a longitudinal direction of the diaper, and the topsheet covering the top surface of the upper core is folded along the rear end of the front core and the front end of the rear core toward the lower core and tucked in between the upper and lower cores.

In the known diaper, a pocket opened from the front waist region toward the crotch region is formed between the front core and the lower core so that feces may be received by the pocket.

However, the diaper disclosed in the above-cited Publication is not provided with a means by which the rear end of the front core and the front end of the rear core are positively spaced upward from the lower core. Consequently, the rear end of the front core and the front end of the rear core are apt to be collapsed onto the lower core and it may be sometimes difficult for the pocket to be sufficiently opened. Even if the pocket is slightly opened, only a small quantity of feces can be received by the pocket, so that the remaining feces may cling to a wearer's skin.

SUMMARY OF THE INVENTION

It is an object of this invention to provide a disposable diaper designed so that a pocket adapted to receive feces can have a sufficient capacity to eliminate an anxiety that the feces might cling to a wearer's skin.

According to this invention, there is provided a disposable diaper comprising a basic absorbent batt structure, a pair of barrier cuffs and at least one supplementary absorbent batt structure. The basic absorbent batt structure having and a liquid-pervious body facing surface and a liquid-impervious garment facing surface, and a front waist region, a rear waist region and a crotch region. The barrier cuffs have proximal edge portions and distal edge portions and extending along transversely opposite sides of the basic absorbent batt structure so as to rise up the body facing surface of the basic absorbent batt structure under tension of the elasticized barrier cuffs. The supplementary absorbent batt structure has a liquid-pervious body facing surface and an opposite surface, and a proximal end portion and a distal end portion and being placed upon the body facing surface of the basic absorbent batt between the barrier cuffs. The proximal end portion lies the front waist region while the distal end portion is supported along transversely opposite side edges of the supplementary absorbent batt structure in a vicinity of the distal end portion by vicinities of the distal edge portions of the barrier cuffs so that the basic and supplementary absorbent batt structures define therebetween a pocket opening from the crotch region toward the front waist region, with and at least the distal end portion except the proximal end portion of the supplementary absorbent batt structure spaced apart upwardly from the body facing surface of the basic absorbent batt structure under tension of the barrier cuffs.

DETAILED DESCRIPTION OF THE PREFERRED EMBODIMENTS

Details of a disposable diaper according to this invention will be more fully understood from the description of the disposable diaper of an open type as a specific embodiment given hereunder with reference to accompanying drawings.

Figure 1:
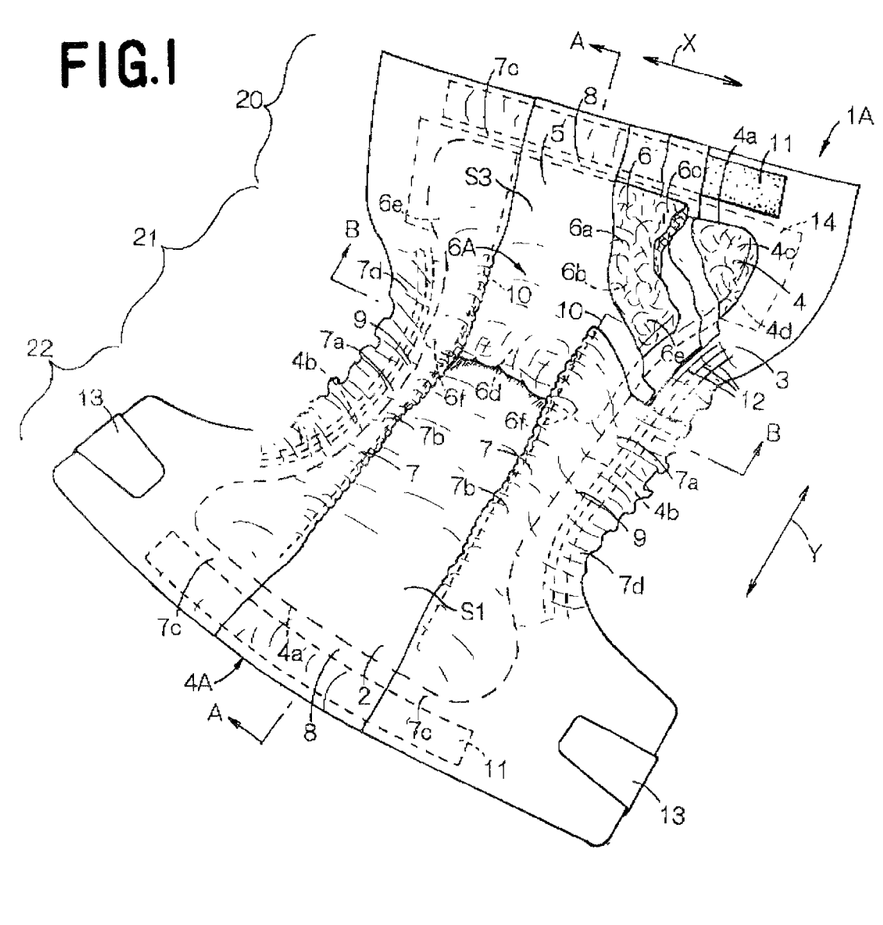
FIG. 1 is a partially cutaway perspective view showing an embodiment of the disposable diaper according to this invention as viewed from the side of the topsheet.
Figure 2:
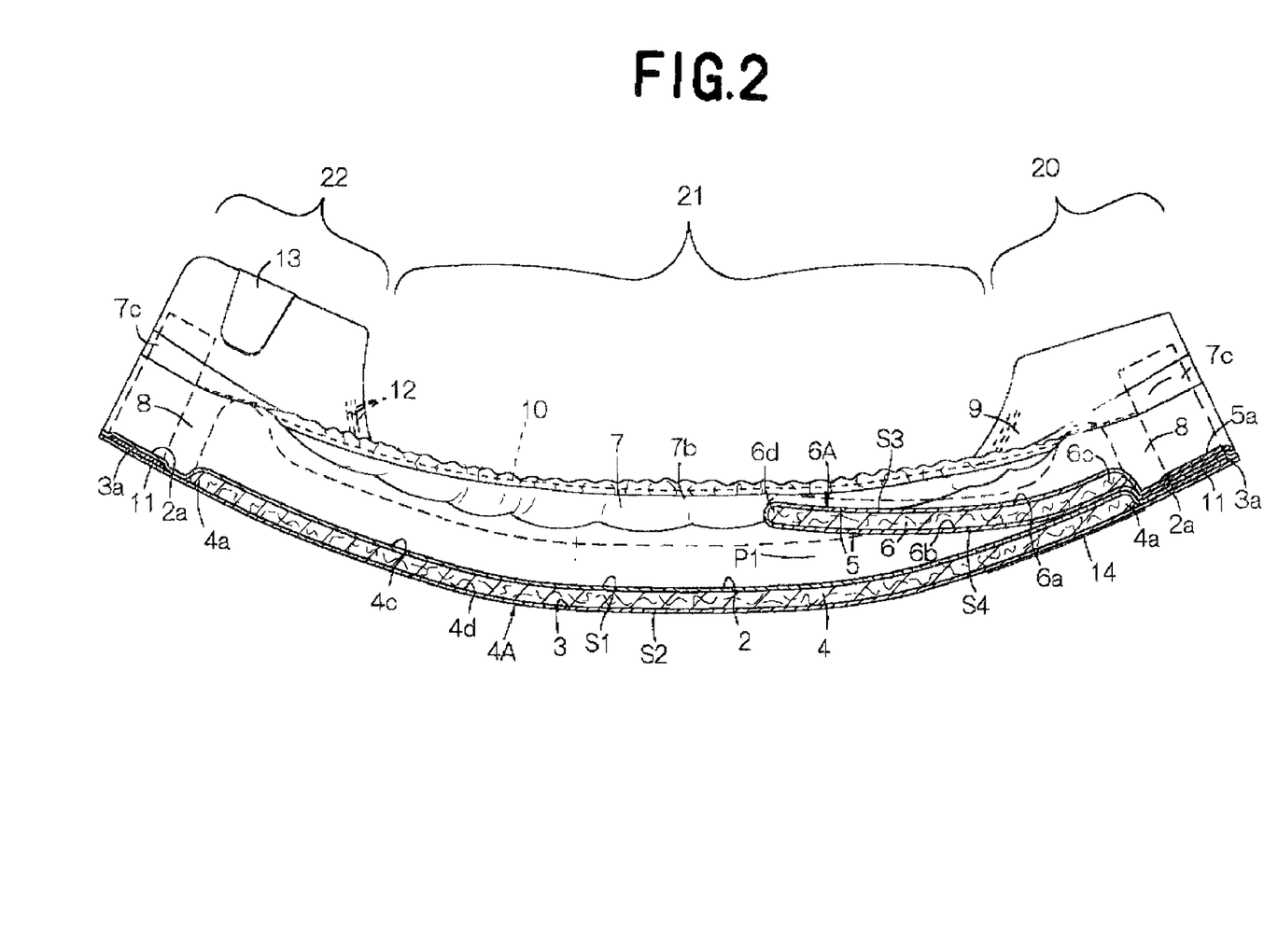
FIG. 2 is a cross-sectional view taken along a line A-A in FIG. 1.
Figure 3:
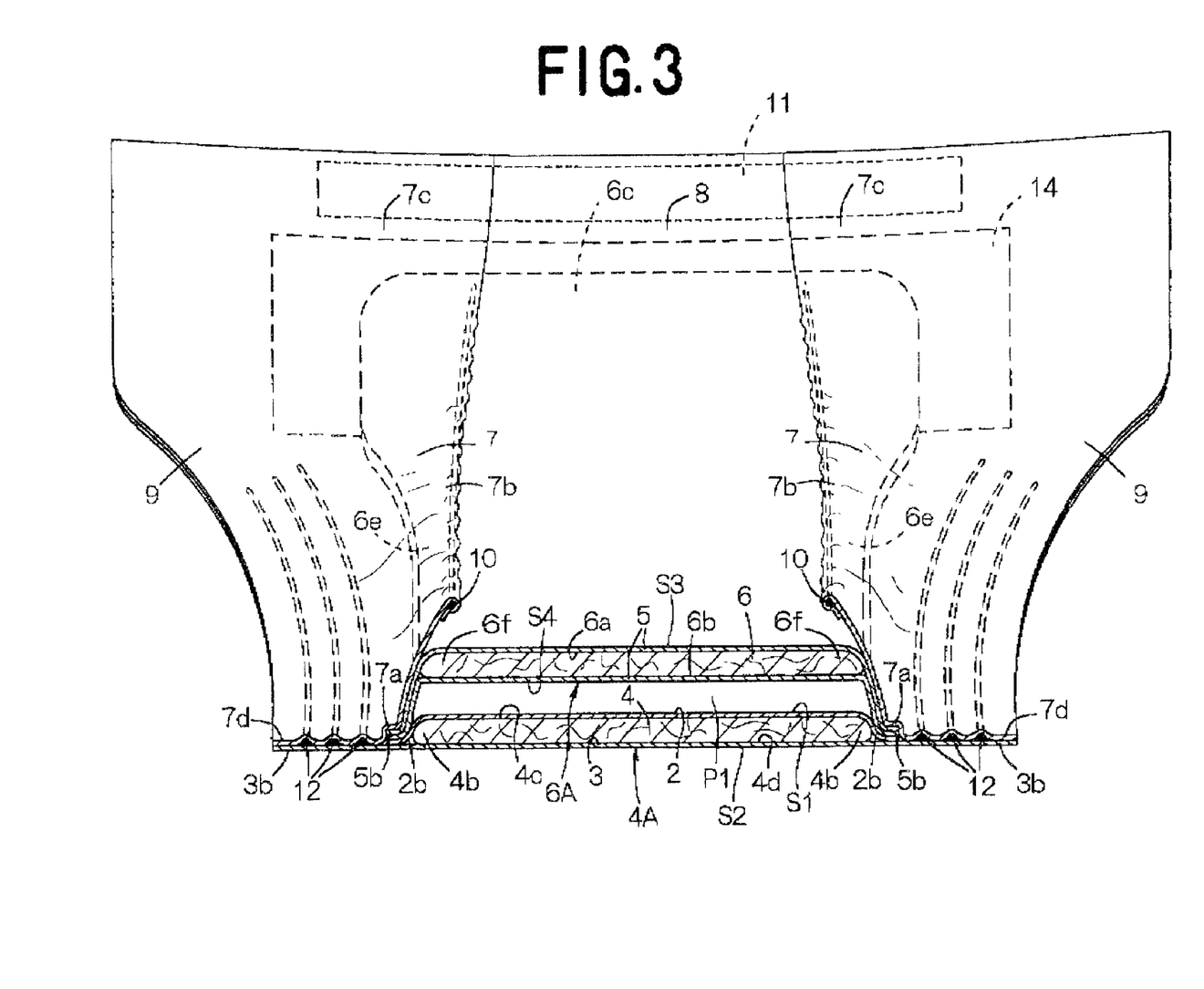
FIG. 3 is a cross-sectional view taken along a line B-B in FIG. 1.
Figure 4:
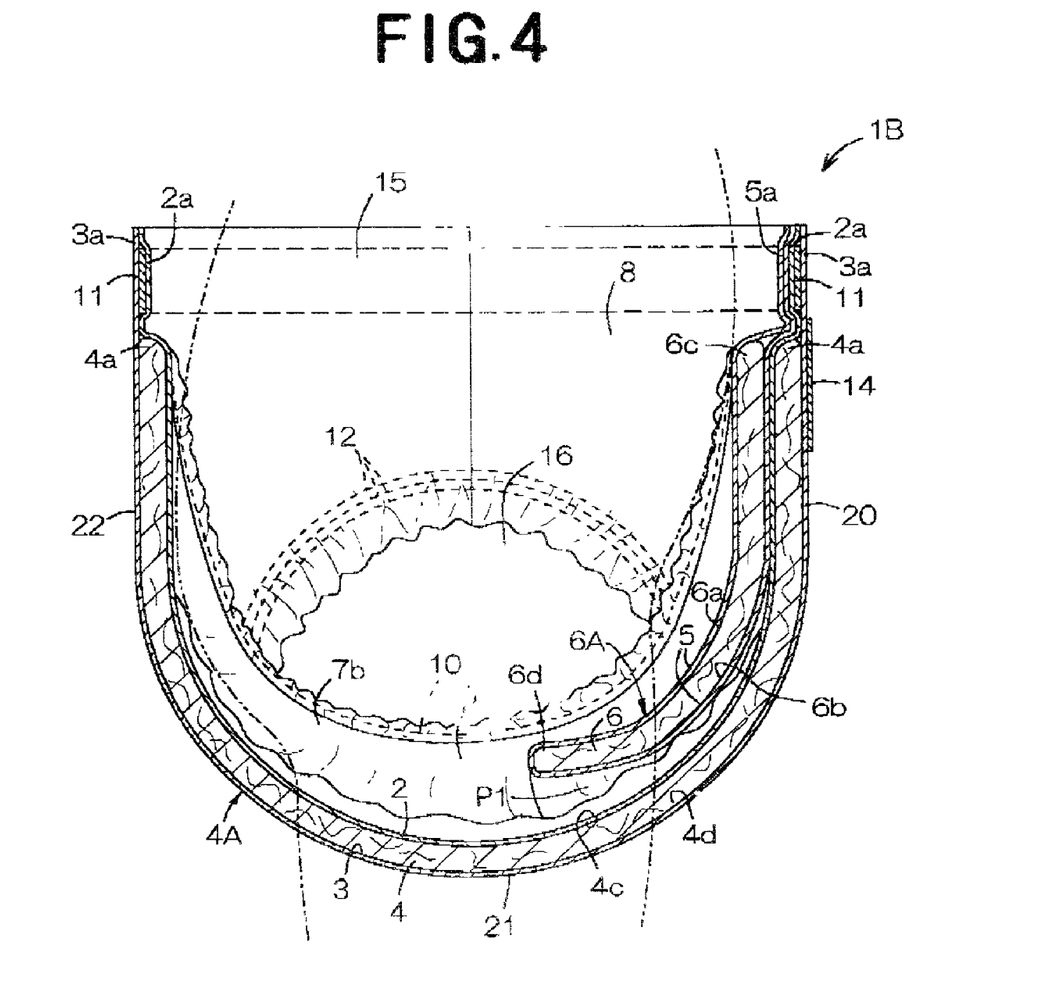
FIG. 4 is a partially cutaway perspective view showing the diaper in FIG. 1 as being worn with front and rear waist regions thereof connected to each other.

FIG. 1 is a partially cutaway perspective view showing a disposable diaper according to an embodiment of this invention as viewed from the side of a liquid-pervious topsheet, FIG. 2 is a cross-sectional view taken along a line A-A in FIG. 1, FIG. 3 is a cross-sectional view taken along a line B-B in FIG. 1 and FIG. 4 is a partially cutaway perspective view showing the diaper 1A of FIG. 1 as being worn with front and rear waist regions 20, 22 thereof connected to each other. In FIG. 1, a transverse direction is indicated by an arrow X and its longitudinal direction of the diaper is indicated by an arrow Y.

A diaper 1A comprises a liquid-pervious topsheet 2 defining a body facing surface S1, a liquid-impervious backsheet 3 defining a garment facing surface S2, a liquid-absorbent first core 4 disposed between these two sheets 2, 3, a liquid-absorbent second core 6 wrapped by the liquid-pervious sheet 5, and barrier cuffs 7 which is substantially liquid-impervious. The topsheet 2, the backsheet 3 and the first core 4 constitute a basic absorbent batt structure 4A, and the sheet 5 and the second core constitutes a supplementary absorbent batt structure 6A.

In the longitudinal direction, the diaper 1A is composed of a front waist region 20, a rear waist region 22 and a crotch region 21 positioned between these front and rear waist regions 20, 22. In the diaper 1A, as is shown in FIG. 1, a pair of end flaps 8 extend in the transverse direction outside longitudinally opposite ends 4a of the first core 4, respectively, and a pair of gasket cuffs 9 extend in the longitudinal direction outside transversely opposite side edges 4b, respectively. In the crotch region 21, the gasket cuffs 9 curve inwardly in the transverse direction of the diaper 1A delineating circular arcs.

As is shown in FIG. 2, the first core 4 has an upper surface 4c and a lower surface 4d. The first core 4 extends across the crotch region 21 into the front and rear waist regions 20, 22. The first core 4 has its upper surface 4c covered with the topsheet 2 to define the body facing surface S1 and its lower surface 4d covered with the backsheet 3 to define the garment facing surface S2. Of the first core 4, the upper surface 4c is joined to the inner surface of the topsheet 2 and the lower surface 4d is joined to the inner surface of the backsheet 3.

As is shown in FIG. 2, the second core 6 is opposed to the upper surface 4c of the first core 4 with the topsheet 2 lying therebetween and extends from the front waist region 20 toward the crotch region 21. The second core 6 has an upper surface 6a and a lower surface 6b, the upper and lower surfaces 6a, 6b being covered with the liquid-pervious sheet 5. Of the second core 6, its upper surface 6a and its lower surface 6b are joined to the inner surface of the liquid-pervious sheet 5. A region of the sheet 5 above the upper surface 6a of the second core 6 defines a body facing surface S3 of the batt structure 6A.

The batt structure 6A has a proximal end portion 6c lying in the front waist region 20 and placed upon the body facing surface S1 of the batt structure 4A, a distal end portion 6d lying in the crotch region 21 and spaced above from the body facing surface S1 of the batt structure 4A by a given dimension and transversely opposite side edges 6e extending in the longitudinal direction between the proximal and distal end portions 6c, 6d. The liquid-pervious sheet 5 is folded back along the distal end portion 6d.

Each of the first and second cores 4, 6 is composed of a mixture of fluff pulp and particles of super-absorptive polymer or a mixture of fluff pulp, particles of a super-absorptive polymer and a thermoplastic synthetic resin fiber, both having been compressed to a desired thickness, for provision of batts. Preferably, the first and second cores 4, 6 are entirely covered with tissue papers to avoid an anxiety that the polymer particles might fall off and/or the cores 4, 6 might be deformed from their initial shapes. The polymer particles may be selected from a group consisting of starch- or cellulose-based polymer and synthetic polymer.

The barrier cuffs 7 lie on the respective gasket cuffs 9 and extend in the longitudinal direction. The barrier cuffs 7 respectively have proximal edge portions 7a extending in the longitudinal direction immediately outside the transversely opposite side edges 4b of the first core 4, distal edge portions 7b extending in parallel to the proximal edge portion 7a and normally biased to rise on the body facing surface S1 of the first core 4, and fixed end portions 7c lying in the front and rear waist regions 20, 22, are collapsed inwardly in the transverse direction of the diaper 1A. Of the barrier cuffs 7, the proximal edge portions 7a are joined to the respective gasket cuffs 9 and the fixed end portions 7c are joined to the respective end flaps 8.

The barrier cuffs 7 further comprise marginal portions 7d extending outwardly from the proximal edge portions 7a in the transverse direction of the diaper 1A. The distal edge portions 7b respectively have elastic members 10 extending in the longitudinal direction and secured under tension thereto. The elastic members 10 are covered with parts of the respective distal edge portions 7b.

With this diaper 1A, the batt structure 6A is joined, at intersections 6f of the distal end portion 6d and the transversely opposite side edges 6e thereof, to the distal edge portions 7b of the respective barrier cuffs 7 with the liquid-pervious sheet 5 lying therebetween. Contraction of the elastic members 10 causes the diaper 1A to curve itself in the longitudinal direction with the topsheet 2 inside and at the same time causes the distal edge portions 7b of the barrier cuffs 7 to uprise on the body facing surface S1 of the batt structure 4A. In the front waist region 20, the distal edge portions 7b of the barrier cuffs 7 raised in this manner lie above the body facing surface S3 of the batt structure 6A.

With this diaper 1A, the distal end portion 6d of the batt structure 6A is lifted above the body facing surface S1 of the batt structure 6A by the distal edge portions 7b of the barrier cuffs 7 raised in the manner described above. Between the batt structures 4A, 6A, a pocket P1 is formed with its opening facing from the crotch region 21 toward the front waist region 20.

The end flaps 8 respectively have ribbon-like elastic members 11 extending in the transverse direction secured under tension so as to be associated with a waist-hole. In the crotch region 21, the gasket cuffs 9 respectively have a plurality of elastic members 12 extending in the longitudinal direction secured under tension so as to be associated with respective leg-holes.

In the rear waist region 22, the barrier cuffs 9 are provided with tape fasteners 13 extending inwardly in the transverse direction of the diaper 1A. The tape fasteners 13 are coated at their free end zones with a self-adhesive (not shown). In the front waist region 20, the backsheet 3 is provided on its outer surface with a rectangular target tape strip 14 made of a plastic film. The target tape strip 14 serves as an engaging for the tape fasteners 13.

In the respective end flaps 8, longitudinally opposite end zones 2a of the topsheet 2 and longitudinally opposite end zones 3a of the backsheet 3 both extending outwardly beyond longitudinally opposite ends 4a of the first core 4 are overlaid and joined to each other as is shown in FIG. 2. Longitudinally opposite end portions 5a of the liquid-pervious sheet 5 which are folded back along the distal end portion 6d of the batt structure 6A and extend outwardly from the proximal end portion 6c of the batt structure 6A in the longitudinal direction are overlaid, joined to each other and then to the end portion 2a of the topsheet 2. The fixed end portions 7c of the respective barrier cuffs 7 are joined to the end portions 5a of the liquid-pervious sheet 5. The elastic members 11 associated with the waist-hole are respectively disposed between the longitudinally opposite end portions 2a of the topsheet 2 and the longitudinally opposite end portions 3a of the backsheet 3 and joined to the end portions 2a, 3a.

In the gasket cuffs 9, transversely opposite side edge zones 2b of the topsheet 2 slightly extend transversely outward beyond the side edges 4b of the first core 4 while transversely opposite side edge zones 3b of the backsheet 3 as well as the marginal portions 7d of the barrier cuffs 7 extend transversely to the outward direction beyond the side edge portions 2b of the topsheet 2, as is shown in FIG. 3. The side edge portions 2b are respectively disposed between the side portions 3b and the marginal portions 7d and joined to the portions 3b, 7d. The side edge portions 3b and the marginal portions 7d are overlaid and joined to each other.

The transversely opposite side edge portions 5b of the liquid-pervious sheet 5 extending transversely outward beyond the side edges 6e of the second core 6 overlaid and joined to each other. These side edge portions 5b are disposed between the side edge portions 2b of the topsheet 2 and the proximal edge portions 7a of the barrier cuffs 7 and joined to the portions 2b, 7a. The elastic members 12 associated with the leg-holes are disposed between the side edge portions 3b of the backsheet 3 and the marginal portions 7d of the cuffs 7 and joined to the portions 3b, 7d.

To wear the diaper 1A, the gasket cuffs 9 in the rear waist region 22 may be overlaid upon the outer surfaces of the gasket cuffs 9 in the front waist region 20 and then the free end portions of the respective tape fasteners 13 may be anchored on the target tape strip 14 by means of a self-adhesive so that the front waist region 20 may be connected to the rear waist region 22. Upon connection of the front and rear waist regions 20, 22, the diaper 1A defines a waist-hole 15 and a pair of leg-holes 16 as is shown in FIG. 4.

With this diaper 1A, the distal end portion 6d of the batt structure 6A is lifted above the body facing surface S1 of the batt structure 4A by the distal edge portions 7b of the barrier cuffs 7 so that the pocket P1 is sufficiently opened to increase its receiving capacity of feces.

With this diaper 1A, even if a large quantity of loose passage or watery feces is discharged on the crotch region 21 and spread on the topsheet 2 into the front waist region 20, most of the discharged feces can be received by the pocket P1 and it is not apprehended that these discharges might leak out from the batt structure 6A. In this way, this diaper 1A can reliably prevent the discharges from clinging to a wearer's skin in the front waist region 20. Of the discharges having been received by the pocket P1, their liquid-portion is absorbed and contained by the batt structure 4A and the batt structure 6A while their solid-portion is contained in the pocket P1.

In the case of this diaper 1A, preferably an absorbing capacity for body wastes per unit area of the batt structure 6A is greater than that of the batt structure 6A. Of body wastes discharged on this diaper 1A, urine is absorbed by the batt structure 6A. The batt structure 6A has an absorbing capacity higher than that of the batt structure 4A and most of urine is absorbed and contained by the batt structure 6A. In other words, there is no anxiety that any quantity of urine might be transferred from the batt structure 6A to the pocket 1 and might be mixed with feces within the pocket P1.

In the diaper 1A, the distal edge portions 7b of the barrier cuffs 7 are elastically biased to uprise and thereby to form barriers against body wastes so that leakage of body wastes possibly occurring beyond the gasket cuffs 9 may be reliably prevented.

Figure 5:
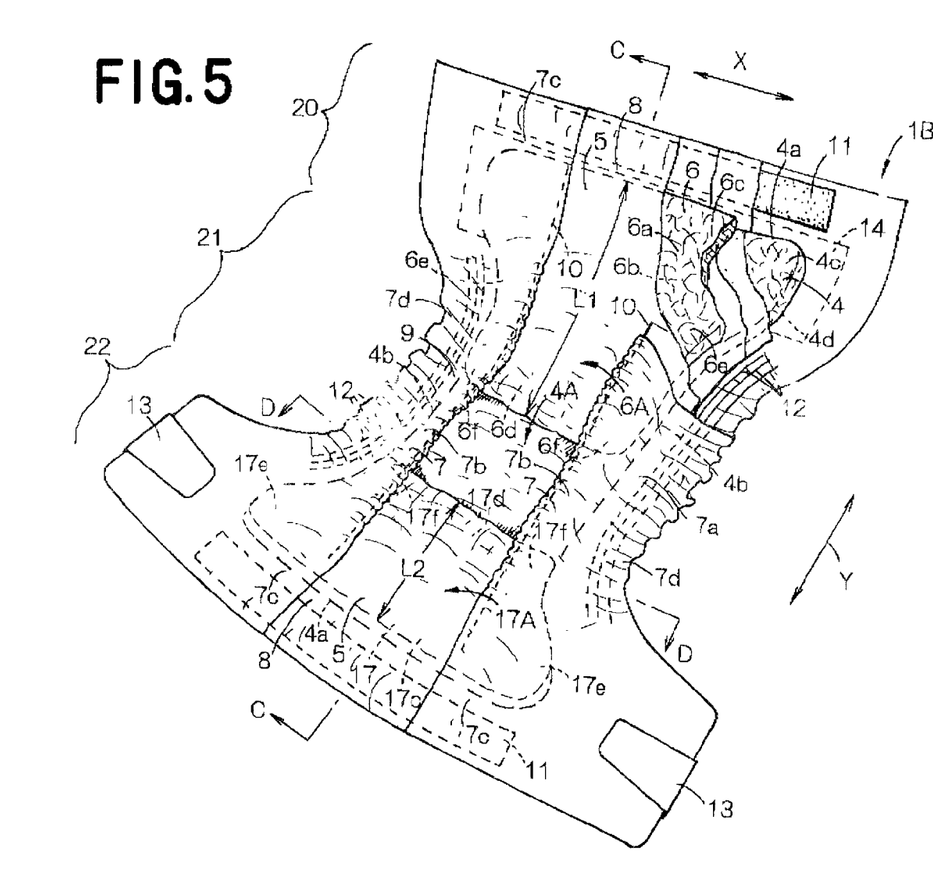
FIG. 5 is a partially cutaway perspective view showing another embodiment of the disposable diaper according to this invention.
Figure 6:
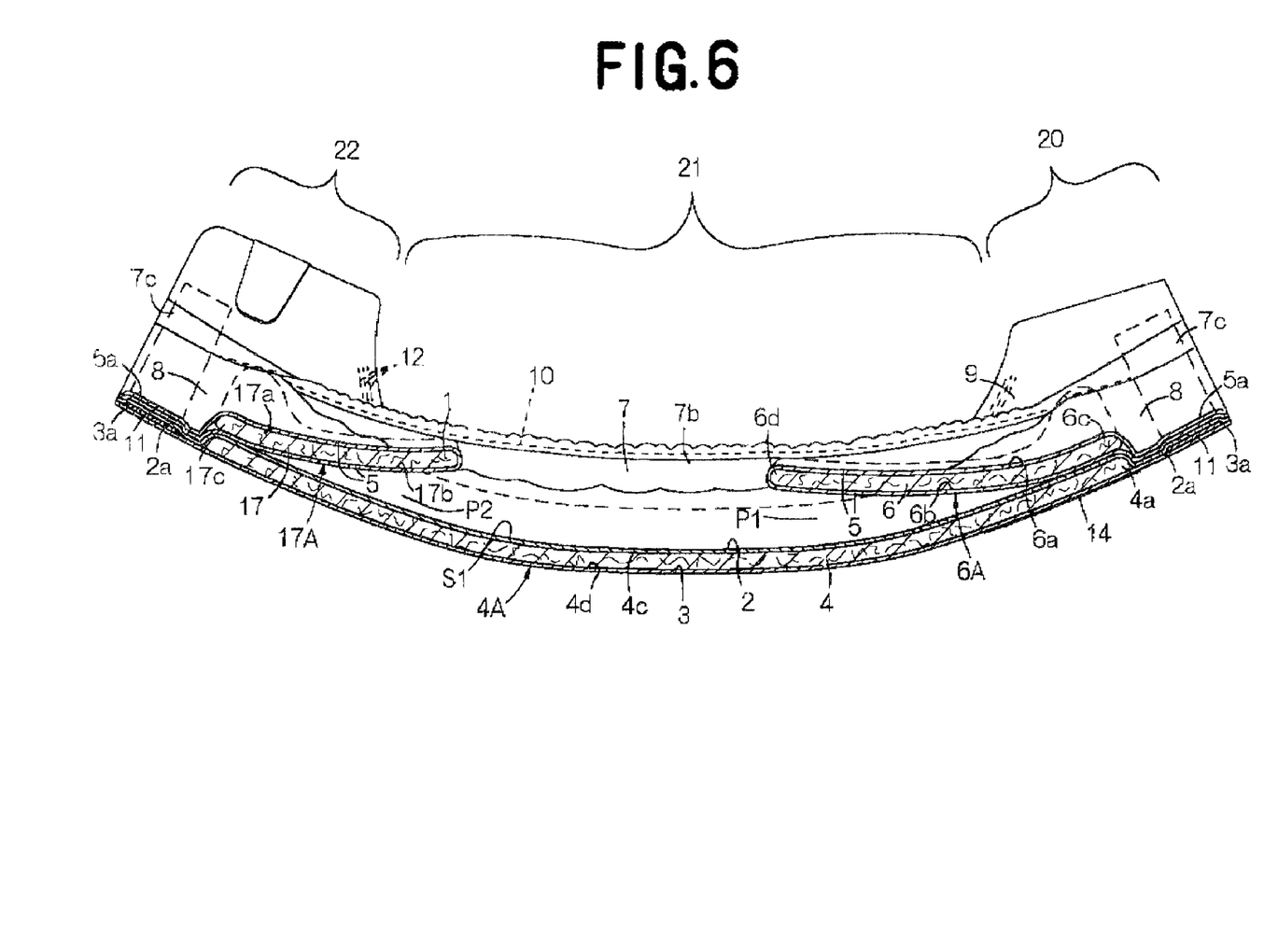
FIG. 6 is a cross-sectional view taken along a line C-C in FIG. 5.
Figure 7:
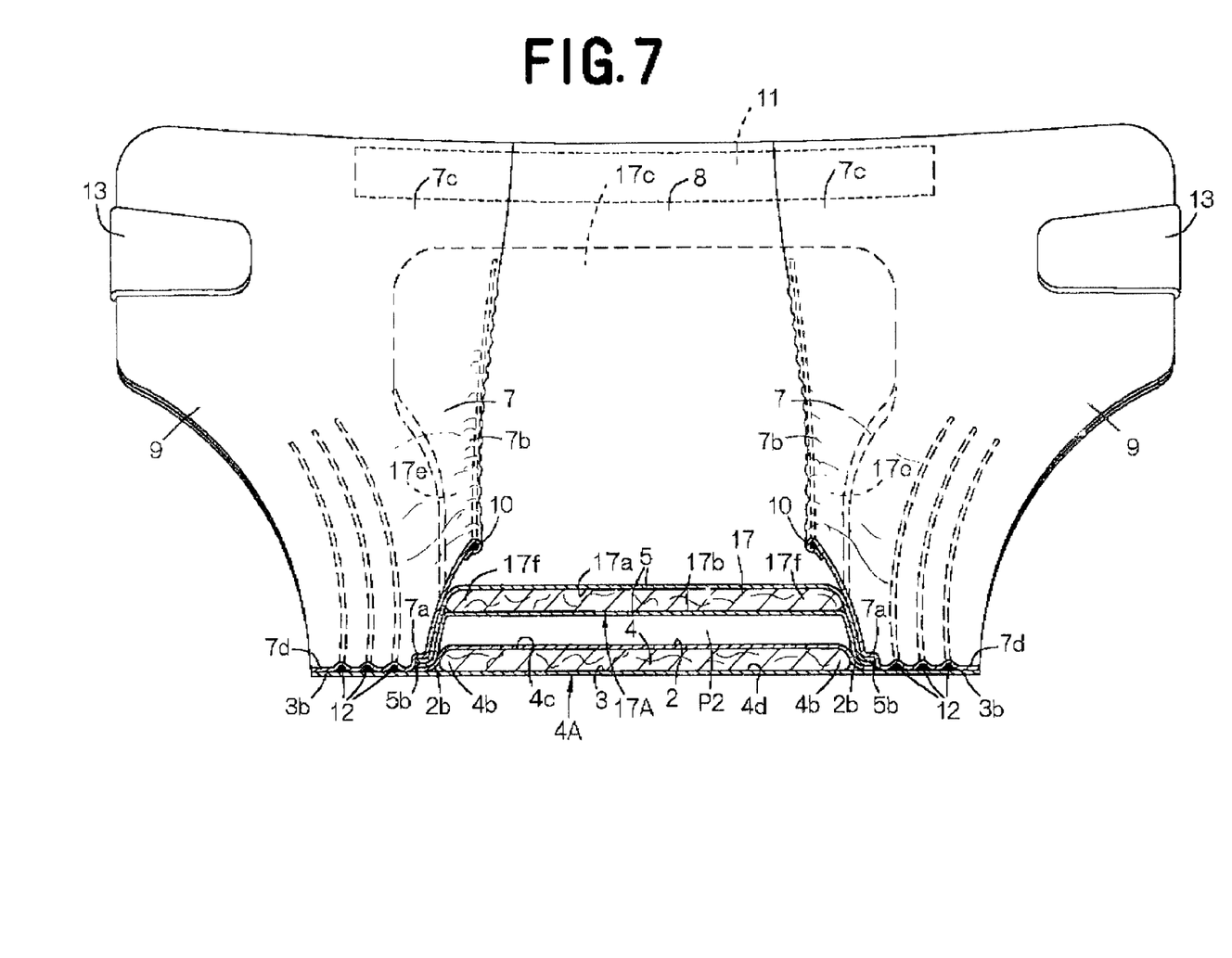
FIG. 7 is a cross-sectional view taken along a line D-D in FIG. 5.
Figure 8:
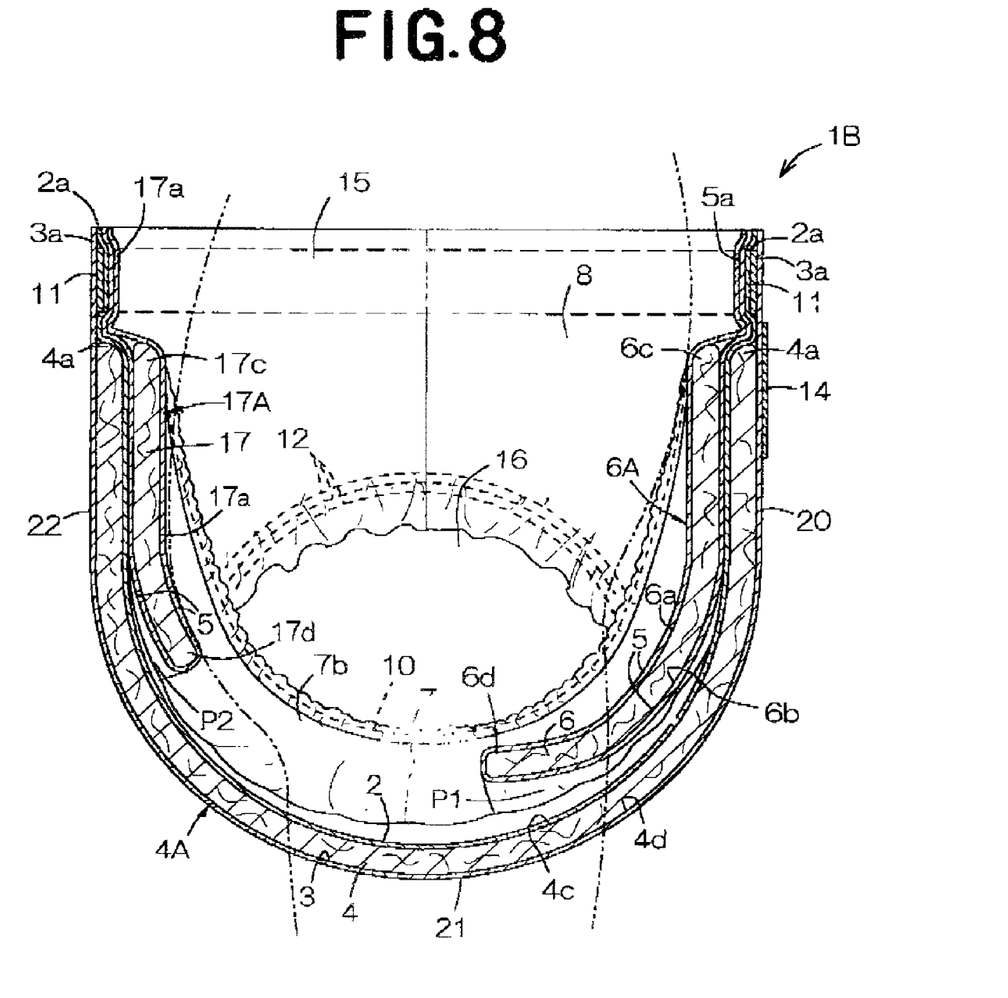
FIG. 8 is a partially cutaway perspective view showing the diaper of FIG. 5 as being worn with front and rear waist regions thereof connected to each other.

FIG. 5 is a partially cutaway perspective view showing another embodiment of a disposable diaper according to this invention, FIG. 6 a cross-sectional view taken along a line C-C in FIG. 5, FIG. 7 is a cross-sectional view taken along a line D-D in FIG. 5 and FIG. 8 is a partially cutaway perspective view showing the diaper 1B of FIG. 5 as being worn with front and rear waist regions 20, 22 thereof connected to each other. A diaper 1B of FIG. 5 is distinguished from that of FIG. 1 in that the diaper 1B includes another supplementary absorbent batt structure 17A having a liquid-absorbent third core 17.

The batt structure 17A lies on the body facing surface S1 of the batt structure 4A and extends from the rear waist region 22 toward the crotch region 21. The third core 17 has an upper surface 17a and a lower surface 17b, both upper and lower surfaces being covered with a liquid-pervious sheet 5. Of this third core 17, the upper surface 17a and the lower surface 17b are joined to the inner surface of the liquid-pervious sheet 5. A region of the sheet 5 above the upper surface 17a of the third core 17 defines a body facing surface.

The batt structure 17A has a proximal end portion 17c lying in the rear waist region 22 and overlaid the batt structure 4A, a distal end portion 17d lying in the crotch region 21 and spaced above from the body facing surface S1 of the batt structure 4A by a given dimension and transversely opposite side edges 17e extending in the longitudinal direction between the proximal and distal end portions 17c, 17d. Along the proximal end portion 17c of the batt structure 17A, the outer surface of the topsheet 2 and the outer surface of the liquid-pervious sheet 5 are joined to each other. The liquid-pervious sheet 5 is folded back along the distal end portion 17d of the batt structure 17A.

The third core 17 is also composed of a mixture of materials similar to those forming the first and second cores 4, 6 and is compressed to a desired thickness. Preferably, the third core 17 is entirely covered with tissue paper.

With this diaper 1B, the batt structure 17A is joined, at intersections 17f of the distal end portion 17d and the transversely opposite side edges 17e thereof, to the distal edge portions 7b of the respective barrier cuffs 7 with the liquid-pervious sheet 5 lying therebetween. In the case of this diaper 1B, a dimension L1 by which the batt structure 6A extends from the front waist region 20 toward the crotch region 21 is larger than a dimension L2 by which the batt structure 17A extends from the rear waist region 22 toward the crotch region 21.

In this diaper 1B, the respective distal end portions 6d, 17d of the batt structure 6A, 17A are spaced from each other in the longitudinal direction by a given dimension in the crotch region 21 so that the body facing surface S1 of the batt structure 4A covered with the topsheet 2 is partially exposed between the distal end portions 6d, 17d. In the crotch region 21, the body facing surface S1 of the batt structure 4A is exposed at a position somewhat aside toward the rear waist region 22. Between the batt structures 4A, 17A, a pocket P2 is formed with its opening facing from the crotch region 21 toward the rear waist region 22.

As is shown in FIG. 6, the opposite end portions 5a of the liquid-pervious sheet 5 which extend outward from the proximal end portion 17c of the batt structure 17A in the longitudinal direction are overlaid, joined to each other and then to the end portion 2a of the topsheet 2. The fixed end portions 7c of the respective barrier cuffs 7 are joined to the end portions 5a of the liquid-pervious sheet 5.

Transversely opposite side edge portions 5b of the liquid-pervious sheet 5 extending transversely outward beyond the side edges 17e of the batt structure 17A are overlaid and joined to each other. The side edge portions 5b are disposed between the side edge portions 2b of the topsheet 2 and the proximal edge portions 7a of the barrier cuffs 7 and joined the portions 2b, 7a.

With this diaper 1B, the distal end portion 17d of the batt structure 17A is lifted above the body facing surface S1 of the batt structure B1 by the distal edge portion 7b of the barrier cuffs 7 raised in the manner as described above. In this way, the pocket 2 is sufficiently opened. This diaper 1B makes it possible to make the feces receiving capacity larger than that of the diaper shown in FIG. 1 and, at the same time, to prevent leakage of feces from the end flaps 8 in the rear waist region 22, since not only the pocket P1 but also the pocket P2 serves to receive feces. With this diaper 1B, it makes it reliably possible to prevent feces from clinging to a wearer's skin in the front waist region 20 as well as in the rear waist region 22.

Figure 9:
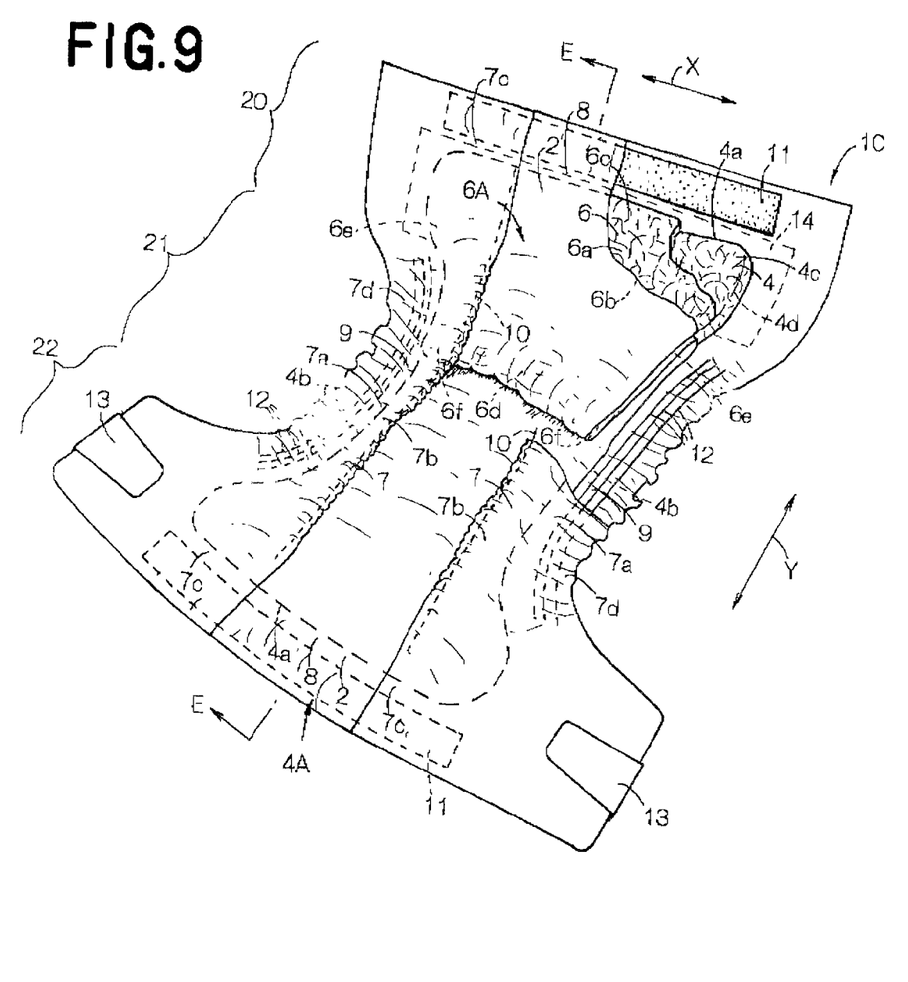
FIG. 9 is a partially cutaway perspective view showing still another embodiment of the disposable diaper according to this invention.
Figure 10:
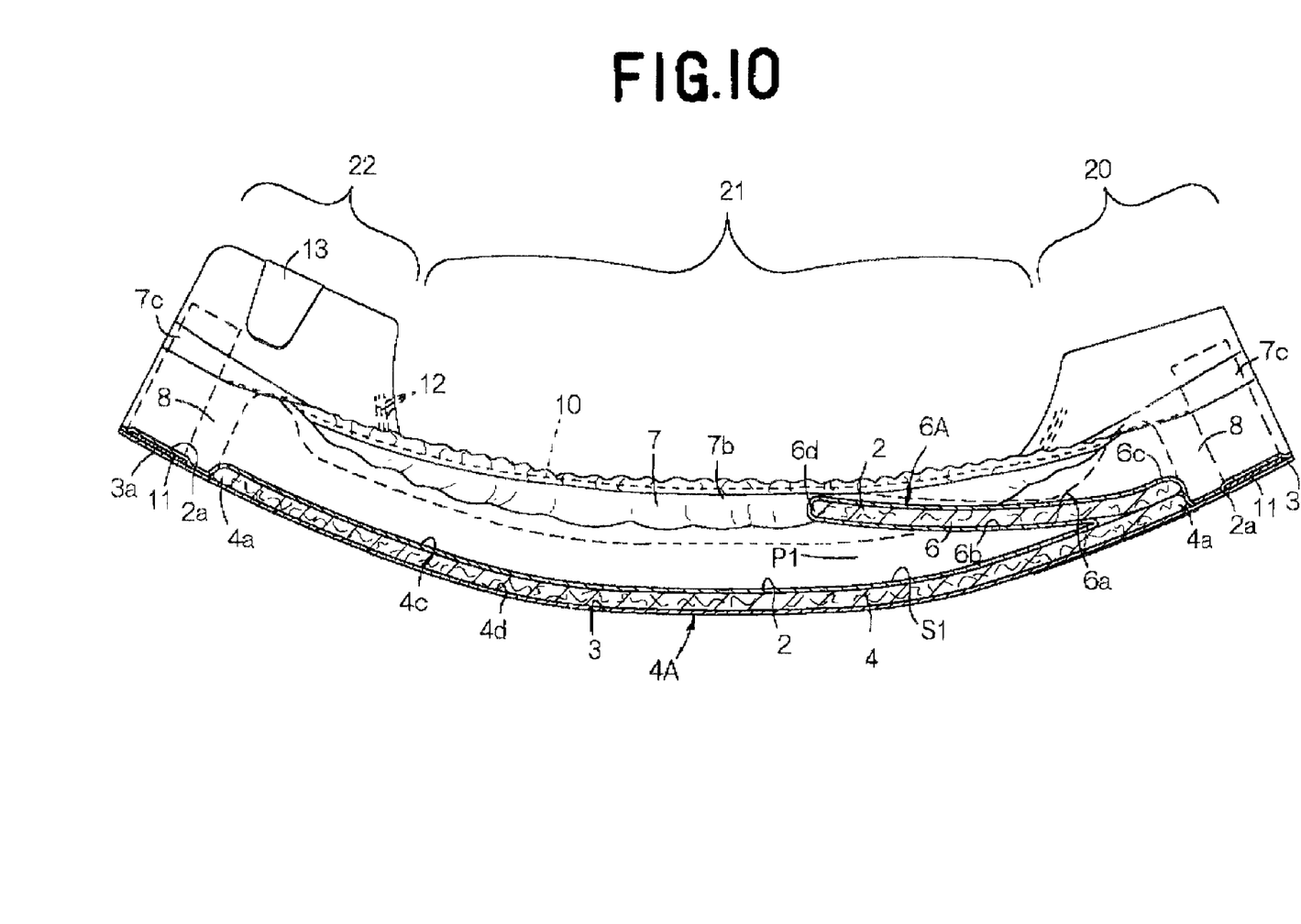
FIG. 10 is a cross-sectional view taken along a line E-E in FIG. 9.

FIG. 9 is a partially cutaway perspective view showing still another embodiment 1C of the disposable diaper according to this invention and FIG. 10 is a cross-sectional view taken along a line E-E in FIG. 9.

In the case of this diaper 1C, the first core 4 of the second core 6 of the batt structure 4A and the batt structure 6A above the batt structure 4A are disposed between the liquid-pervious topsheet 2 and the liquid-impervious backsheet 3. The topsheet 2 is folded back along the distal end portion 6d of the batt structure 6A onto the lower surface 6b of the second core 6 and tucked in between the upper surface 4c of the first core 4 and the lower surface 6b of the second core 6. Along the proximal end portion 6c of the batt structure 6A, the upper surface 4c of the first core 4 and the lower surface 6b of the second core 6 are joined to each other.

In this diaper 1C, the upper surface 6a of the second core 6 is covered with the topsheet 2, and the lower surface 6b of the second core 6 except the proximal end portion 6c as well as the upper surface 4c of the first core 4 are covered with the topsheet 2. The topsheet 2 is joined to the surfaces 4c, 6a, 6b.

In the case of this diaper 1C, the batt structure 6A is joined, at intersections 6f of the distal end portion 6d and the transversely opposite side edges 6e thereof, to the distal edge portions 7b of the respective barrier cuffs 7 with the topsheet 2 lying therebetween. The pocket P1 opening from the front waist region 20 toward the crotch region 21 is formed between the batt structure 4A, 6A.

It is also possible to arrange this diaper 1C in a similar manner to the diaper 1B shown in FIG. 5 so that the batt structure 17A extends from the rear waist region 22 toward the crotch region 21 on the body facing surface S1 of the batt structure 4A with the first core 4 of the batt structure 4A and the third core 17 of the batt structure 17A disposed between the top- and backsheets 2, 3. With the arrangement including the batt structure 17A in this manner, the topsheet 2 will be folded back along the distal end portion 17d onto the lower surface 17b of the third core 17 and tucked in between the upper surface 4c of the first core 4 and the lower surface 17b of the third core 17. The batt structure 17A will be joined, at the intersections 17f of the distal end portion 17d of the batt structure 17A and the opposite side edges 17e, to the distal end portions 7b of the barrier cuffs 7 with the topsheet 2 lying therebetween.

The topsheet 2 and the liquid-pervious sheet 5 may be formed using a hydrophilic fibrous nonwoven fabric or a finely apertured plastic film. The backsheet 3 may be formed using any one selected from a group consisting of a hydrophobic fibrous nonwoven fabric, a liquid-impervious plastic film, a two-layered hydrophobic fibrous nonwoven fabric and a composite sheet comprising hydrophobic fibrous nonwoven fabric and a plastic film bonded together. The barrier cuffs 7 may be formed using a hydrophobic fibrous nonwoven fabric.

It is also possible to use a composite nonwoven fabric comprising a melt blown fibrous nonwoven fabric of a high water-resistance sandwiched between two layers of spun bond fibrous nonwoven fabric of a high strength and a high flexibility.

The nonwoven fabric may be selected from a group including spun lace-, needle punch-, melt blown-, thermal bond-, spun bond-, chemical bond- and air through-nonwoven fabrics. Component fiber of the nonwoven fabric may be selected from a group including polyolefine-, polyester- and polyamide-based fibers and polyethylene/polypropylene or polyethylene/polyester core-sheath type conjugated fiber and side-by-side type conjugated fiber.

Joining of the top- and backsheets 2, 3 and the barrier cuffs 7 one to another, joining the cores 4, 6, 17 to these sheets 2, 3, 5 as well as attaching the elastic members 10, 11, 12 may be carried out using a suitable adhesive such as a hot melt adhesive or technique of welding such as sonic-sealing or heat-sealing.

This invention is applicable not only to an open-type diaper but also to a pants-type diaper having front and rear waist regions previously connected to each other.

The disposable diaper according to this invention enables the pocket defined between the basic and supplementary absorbent batt structure to be opened from the crotch region toward the front waist region to provide increased feces receiving capacity, since distal end portion of the supplementary absorbent batt structure is lifted above the body facing surface of the basic absorbent batt structure by the elastically raised distal end portions o the barrier cuffs. In this way, this diaper can receive a large quantity of feces within the pocket and prevent any quantity of feces from leaking to the supplementary absorbent batt structure. There is no anxiety that any quantity of feces might cling to a wearer's skin in the front waist region.

With the diaper arranged so that the supplementary absorbent batt structure has a urine receiving capacity per unit area higher than that of the basic absorbent batt structure, most of urine is absorbed and contained by the supplementary absorbent batt structure without apprehension that a certain quantity of urine might be transferred from the supplementary absorbent batt structure to the pocket and mixed with feces.

With this diaper having a second supplementary absorbent batt structure, the second supplementary absorbent batt structure is lifted above the body facing surface of the basic absorbent batt structure by the elastically raised distal end portion of the barrier cuffs. Consequently, the pocket is defined between the basic and second supplementary absorbent batt structure and sufficiently opened from the rear waist region toward the crotch region. Such diaper makes it possible to receive feces in this pocket having a sufficient capacity to prevent a leak of feces from possibly occurring beyond the end flaps in the rear waist region. With this diaper, there is no anxiety that any quantity of feces might cling to a wearer's skin in the front waist region as well as in the rear waist region.

What is claimed is:

1. A disposable diaper comprising:
   a primary absorbent batt structure;
   a pair of barrier cuffs;
   at least one supplementary absorbent batt assembly;
   said primary batt assembly including a liquid-pervious body facing surface, a liquid-impervious garment facing surface, a front waist region, a rear waist region, and a crotch region;
   said barrier cuffs having proximal edge portions and distal edge portions and extending along transversely opposite sides of said primary absorbent batt assembly so as to have a height and rise up from said body facing surface of said primary absorbent batt assembly under tension of said barrier cuffs; and
   said supplementary absorbent batt assembly having a liquid-pervious body facing surface, an opposite surface, a proximal end portion, and a distal end portion,
   said supplementary absorbent batt assembly being placed upon said body facing surface of said primary absorbent batt assembly between said barrier cuffs, said proximal end portion lying in said front waist region and said distal end portion being supported along transversely opposite side edges of said supplementary absorbent batt assembly in a vicinity of said distal edge portion by portions of said distal edge portions of said barrier cuffs so that said primary and supplementary absorbent batt assemblies define therebetween a pocket opening from said crotch region toward said front waist region, with at least said distal end portion and said opposite side edges of said supplementary absorbent batt assembly spaced apart upwardly from said body facing surface of said primary absorbent batt assembly by a portion of the height of said barrier cuffs which separate said supplementary batt from said primary absorbent batt under tension of said barrier cuffs.

2. A disposable diaper according to claim 1, wherein said primary absorbent batt assembly comprises a liquid-pervious topsheet defining said body facing surface thereof, a liquid-impervious backsheet defining said garment facing surface thereof and a liquid-absorbent first core disposed between said liquid-pervious topsheet and said liquid-impervious backsheet.

3. A disposable diaper according to claim 1, wherein said supplementary absorbent batt assembly comprises a liquid-absorbent second core and a liquid-pervious sheet covering at least a body facing surface of said liquid-absorbent second core.

4. A disposable diaper according to claim 1, wherein said barrier cuffs include elastic members secured along said distal end portions thereof.

5. A disposable diaper according to claim 1, wherein said distal end portions of said barrier cuffs are positioned inwardly of said proximal end portions of said barrier cuffs.

6. A disposable diaper according to claim 2, wherein said primary absorbent batt assembly comprises a pair of elasticized gasket cuffs extending outwardly from transversely opposite side edges of said liquid-absorbent first core.

7. A disposable diaper according to claim 6, wherein said elasticized gasket cuffs include elastic members secured therealong.

8. A disposable diaper according to claim 6, wherein said proximal end portions of said barrier cuffs are joined onto said elasticized gasket cuffs.

9. A disposable diaper according to claim 1, wherein an absorbing capacity per unit for body wastes of said supplementary absorbent batt assembly is greater than an absorbing capacity per unit for body wastes of said primary absorbent batt assembly.

10. A disposable diaper according to claim 1, wherein said diaper further comprises a second supplementary absorbent batt assembly having a body facing surface covered with a liquid-pervious sheet, said second supplementary absorbent batt assembly lying on the body facing surface of said primary absorbent batt assembly;

said second supplementary absorbent batt assembly having a proximal end portion lying in said rear waist region so as to be placed upon said primary absorbent batt assembly, a distal end portion lying in said crotch region and spaced upward from said primary absorbent batt assembly;

said second supplementary absorbent batt assembly being connected, along transversely opposite side edges thereof, to the said distal edge portions of said barrier cuffs with said liquid-pervious sheet lying therebetween so that said primary and second supplementary absorbent batt assemblies form therebetween a pocket opening from said crotch region toward said rear waist region; and said distal end portions of said supplementary absorbent batt and said second supplementary batt assemblies are spaced apart from each other by a dimension in a longitudinal direction of the diaper so that said body facing surface of said primary absorbent batt assembly is partially exposed between said distal end portions of said supplementary absorbent batt and said secondary absorbent batt assemblies.

11. A disposable diaper according to claim 10, wherein a dimension by which said supplementary absorbent batt assembly extends from said front waist region to said crotch region is larger than a dimension by that which said second supplementary absorbent batt assembly extends from said rear waist region to said crotch region and said body facing surface of said primary absorbent batt assembly is exposed in said crotch region at a position toward said rear waist region.

* * * * *